United States Patent
Hwang et al.

US008383767B2

(10) Patent No.: US 8,383,767 B2
(45) Date of Patent: Feb. 26, 2013

(54) IMMUNOGENIC PROTEIN CARRIER CONTAINING AN ANTIGEN PRESENTING CELL BINDING DOMAIN AND A CYSTEINE-RICH DOMAIN

(75) Inventors: Jaulang Hwang, Taipei (TW); Chun-Cheng Lin, Fongyuan (TW); Hsiao-Ling Chiang, Taichung County (TW); Fan-Dan Jan, Chiayi County (TW); Chiao-En Chen, Taichung County (TW); Chia-Tse Shu, Tainan County (TW)

(73) Assignee: Academia Sinica, Taipei (TW)

( * ) Notice: Subject to any disclaimer, the term of this patent is extended or adjusted under 35 U.S.C. 154(b) by 650 days.

(21) Appl. No.: 12/491,521

(22) Filed: Jun. 25, 2009

(65) Prior Publication Data
US 2009/0324619 A1    Dec. 31, 2009

Related U.S. Application Data

(60) Provisional application No. 61/076,153, filed on Jun. 27, 2008.

(51) Int. Cl.
| | |
|---|---|
| A61K 38/00 | (2006.01) |
| A61K 39/00 | (2006.01) |
| A61K 39/38 | (2006.01) |
| A61K 45/00 | (2006.01) |
| A61K 47/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |

(52) U.S. Cl. .................. 530/300; 424/184.1; 424/278.1
(58) Field of Classification Search ........................ None
See application file for complete search history.

(56) References Cited

U.S. PATENT DOCUMENTS
6,838,553 B1    1/2005 Hwang et al.
2004/0057958 A1*   3/2004 Waggoner et al. ......... 424/184.1

FOREIGN PATENT DOCUMENTS
WO    WO 0055180 A2 *    9/2000
WO    WO 0107081 A1 *    2/2001

OTHER PUBLICATIONS

Genbank AAA 61201.1, 1995, pp. 1-2.*
Orlinick et al., 1997, J. Biol. Chem. vol. 272: 28889-28894.*
Brockhausen, Inka, "Mucin-Type O-Glycans in Human Colon and Breast CancerL Glycodynamics and Functions," European Molecular Biology Organization, 7(6):599-604 (2006).
Ogata et al., "Different Modes of Sialyl-Tn Expression During Malignant Transformation of Human Colonic Mucosa," Glycoconjugate Journal, 15:29-35 (1998).
Itzkowitz et al., "A Novel Mucin Antigen Associated with Prognosis in Colorectal Cancer Patients," Cancer, 66:1960-1966 (1990).
Itzkowitz et al., "Expression of TN, Sialosyl-Tn, and T Antigens in Human Colon Cancer," Cancer Research, 49: 197-204 (1989).
Dabelsteen, Erik, "Cell Surface Carbohydrates as Prognostic Markers in Human Carcinomas," Journal of Pathology, 179:358-369 (1996).
Zhang et al., "Expression of Potential Target Antigens for Immunotherapy on Primary and Metastatic Prostate Cancers," Clinical Cancer Research, 4:295-302 (1998).
Slovin et al., "Fully Synthetic Carbohydrate-Based Vaccines in Biochemically Relapsed Prostate Cancer: Clinical Trial Results with a α-N-Acetylgalactosamine-O-Serine/Threonine Conjugate Vaccine," Journal of Clinical Oncology, 21(23):4292-4298 (2003).
Harikomori et al., "Glycosphingolipid Antigens and Cancer Therapy," Chemistry and Biology, 4:97-104 (1997).
Hsu et al., "Vaccination Against Gonadotropin-Releasing Hormone (GnRH) Using Toxin Receptor-binding Domain-conjugated GnRH Repeats," Cancer Research, 60:3701-3705 (2000).
Chiang, Hsiao-Ling; Development of the carrier for the preparation of potent carbohydrate immunogen; Master Thesis, 2006.

* cited by examiner

Primary Examiner — Amy Juedes
(74) Attorney, Agent, or Firm — Occhiuti Rohlicek & Tsao LLP

(57) ABSTRACT

A protein carrier containing an antigen presenting cell binding domain and a cysteine-rich domain. Also described herein is an immunoconjugate containing the protein carrier with an antigen conjugated to multiple cysteine residues in the cysteine-rich domain, and an immune composition containing the immunoconjugate and an adjuvant, as well as their uses in eliciting immune responses.

23 Claims, 4 Drawing Sheets

Scheme 3

US 8,383,767 B2

IMMUNOGENIC PROTEIN CARRIER CONTAINING AN ANTIGEN PRESENTING CELL BINDING DOMAIN AND A CYSTEINE-RICH DOMAIN

RELATED APPLICATION

This application claims priority to U.S. Provisional Application No. 61/076,153, filed on Jun. 27, 2008, the content of which is hereby incorporated by reference in its entirety.

BACKGROUND OF THE INVENTION

Certain glycoantigens, e.g., Tn, sTn, GM2, and Globo H, have been found to be overly expressed on cancer cells. These antigens, particularly their sugar epitopes, are targets in cancer diagnosis and immune therapy.

As sugar epitopes typically have low immunogenicity, they are routinely conjugated with keyhole limpet hemocyanin (KLH) or bovine serum albumin (BSA) as a protein carrier to elicit strong immune responses. However, this approach has at least two disadvantages. First, the conjugation efficiency between KLH/BSA and a sugar epitope is generally low. Second, the resultant conjugate would elicit immune responses not specific to the sugar epitope.

There is a need for a new approach to improve immunogenicity of a low-antigenic molecule.

SUMMARY OF THE INVENTION

The present invention is based on an unexpected discovery that coupling a glycoantigen Tn, sTn, or GM3 with a protein carrier containing an immunoglobulin (Ig) Fc domain and a cysteine-rich domain significantly improved its antigenecity.

Accordingly, one aspect of this invention relates to a non-naturally occurring polypeptide containing an antigen presenting cell (APC) binding domain and a cysteine-rich domain. The APC binding domain is either an Ig Fc fragment (e.g., the Fc fragment of a human Ig) or a receptor binding domain of a toxin (e.g., Pseudomona exotoxin A, tetanus toxin, or cholera toxin). The cysteine-rich domain contains one or more copies (e.g., 2-30) of a 10-amino acid (10-aa) fragment, in which at least 3 (e.g., 6) residues are cysteines. In one example, the 10-aa fragment has the amino acid sequence of Pro-Cys-Cys-Gly-Cys-Cys-Gly-Cys-Gly-Cys (SEQ ID NO: 1) and the cysteine-rich domain includes 7 copies of this fragment in tandem repeat. Also described herein is a nucleic acid (e.g., an expression vector) including a nucleotide sequence that encodes the polypeptide of this invention and a host cell containing the nucleic acid.

Another aspect of this invention relates to an immunoconjugate containing the polypeptide described above conjugated with an antigen (e.g., sTn, Tn, TF, GM2, GM3, phosphoserine, phosphothreonine, sialic acid, N-acetylglucosamine, Globo H, Lewis x, Lewis y, or a steroid hormone). At least 3 cysteine residues in the cysteine-rich domain are conjugated with the antigen. This immunoconjugate can be mixed with an adjuvant to generate an immune composition. When the antigen is cancer-associated (e.g., sTn, Tn, TF, GM2, GM3, Globo H, Lewis x, Lewis y, or a sex hormone), the immune composition can be used for treating cancer (e.g., prostate cancer, breast cancer, cervical cancer, liver cancer, kidney cancer, colon cancer, lung cancer, or ovary cancer).

In yet another aspect, the present invention features a method of inducing an immune response in a subject (e.g., a human or a non-human mammal) by administering to the subject an effective amount of the immunoconjugate or the immune composition described above. In one example, the immune response is production of an antibody that specifically binds to the antigen contained in the immunoconjugate and the subject is a non-human mammal, such as mouse, rat, rabbit, sheep, goat, or horse. The antibody can be isolated from the serum of the subject.

Also within the scope of this invention is use of the immunoconjugate or the immune composition described above in inducing an immune response, treating a disease (e.g., cancer), or manufacturing a medicament (e.g., a vaccine) in treating the disease.

The details of one or more embodiments of the invention are set forth in the description below. Other features or advantages of the present invention will be apparent from the following drawings and detailed description of several examples, and also from the appended claims.

BRIEF DESCRIPTION OF THE DRAWINGS

The drawings are first described.

DETAILED DESCRIPTION OF THE INVENTION

Described herein is a protein carrier capable of conjugating with an antigen, particularly a low-immunogenic molecule, in clustered form. This protein carrier contains two domains: (1) an APC binding domain and (2) a cysteine-rich domain.

The APC binding domain is a ligand that interacts with a receptor of APC (e.g., dendritic cell, macrophage, or B lymphocyte, and consequently, triggers endocytosis). APC receptors and their cognate ligands are well known in the art. See, e.g., Abbas et al., Cellular and Molecular Immunology, $4^{th}$ ed, W. B. Saunders, pp 500-514. The APC binding domain described herein can be a Fc fragment of an Ig, such as a human Ig (i.e., IgA, IgE, IgD, IgG, or IgM) or an Ig of a non-mammal (e.g., mouse, rat, rabbit, sheep, goat, or horse). The APC binding domain can also be a receptor binding domain of a toxin. The term "toxin" used herein refers to a microorganism polypeptide responsible for pathogenesis via interaction with its cognate cellular receptor. Its receptor binding domain is a fragment thereof that binds to the cognate cellular receptor of the toxin. The receptor binding domains of many toxins, e.g., Pseudomonas exotoxin A, diptheria toxin, or tenatus toxin, are well known in the art. See, e.g., U.S. Pat. No. 6,838,553.

Figure 1:
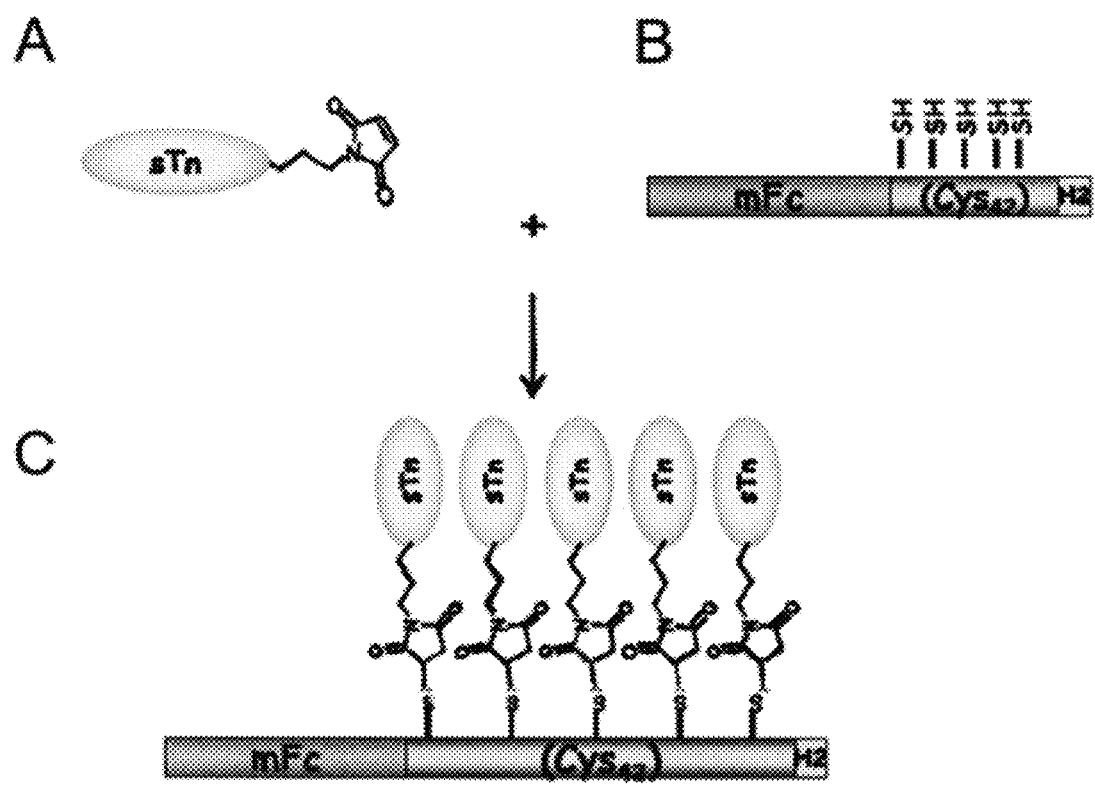
FIG. 1 is a diagram showing a process of conjugating antigen sTn to a protein carrier via a maleimide linker. The protein carrier contains a Fc fragment of a mouse immunoglobulin, a cysteine-rich domain containing 42 cysteine residues, and two repeats of a His-tag.

The cysteine-rich domain contains one or more copies of a 10-aa fragment that includes at least 3 cysteine residues. When multiple copies are included, they can be in tandem repeat. In one example, this cysteine-rich domain includes 42 cysteine residues. The thio-groups in these cysteine residues serve as anchors for antigen conjugation. Given the multiplicity of the thio-groups in this domain, it can conjugate with multiple molecules of an antigen in cluster. See FIG. 1.

The protein carrier described herein can be prepared by conventional recombinant technology. An example follows. A nucleotide sequence encoding the cysteine-rich domain can be prepared by the template-repeat PCR technology well known in the art. It is then linked to another nucleotide sequence encoding an APC binding domain, preferably at its 3' end, to produce a nucleotide sequence encoding the protein carrier. This nucleotide sequence, cloned into an expression vector, is introduced into a suitable host cell for expression of the protein carrier. Preferably, the expression vector contains a nucleotide sequence encoding a protein tag, e.g., His-tag or glutathione-S-transferase, which, when fused with the protein carrier, facilitates its purification. If desired, the protein tag can be removed by, e.g., enzymatic digestion.

Any antigen, particularly that of low immunogenicity, can be conjugated with the protein carrier described above by forming covalent bonds with multiple cysteine residues in the cysteine-rich domain, to produce an immunoconjugate. Exemplary antigens include, but are not limited to, glycotopes (e.g., Tn, sTn, GM2, and GM3), glycolipids (e.g., Globo H and SSEA3), and glycophingolipids (e.g., B-I and B-II). The antigen can also be a steroid hormone, such as a glucocorticoid (e.g., prednisone, dexamethasone, or triamcinolone), a mineralocorticoid (e.g., fludrocortisone), a vitamin D (e.g., dihydrotachysterol), an androgen (e.g., oxandrolone or nandrolone), an estrogen (e.g., diethylstilbestrol), or a progestins (e.g., norethindrone or medroxyprogesterone acetate). Androgens and estrogens taken together are known as sex hormones.

Figure 2:
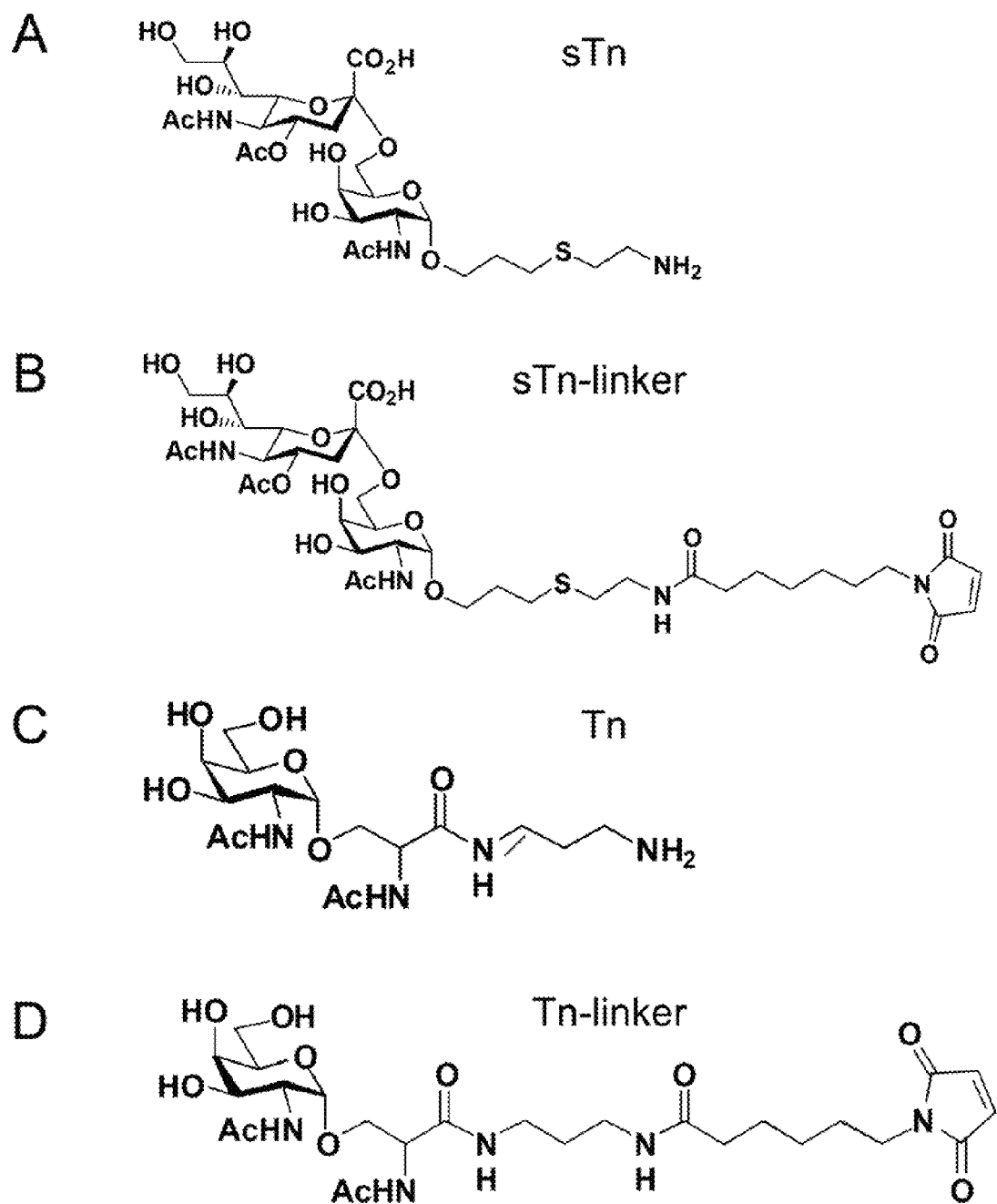
FIG. 2 is a diagram showing the structures of glycoepitope sTn and Tn, and their linkage with a maleimide linker.

Preferably, an antigen is conjugated with the protein carrier via a linker (e.g., a maleimide linker capable of reacting with both an amine group and a thio group). See FIGS. 1 and 2. Examples are N-e-Maleimidocaproic acid, m-Maleimidobenzoyl-N-hydroxysuccinimide ester, N-e-Maleimidocaproyloxy]succinimide ester, and succinimidyl-6-[β-maleimidopropionamido]-hexanoate.

The immunoconjugate of this invention can be used in preparation of an immune composition (e.g., a vaccine), following methods well known in the art. See, e.g., U.S. Pat. Nos. 4,601,903; 4,599,231; 4,599,230; and 4,596,792. It can be mixed with an adjuvant (e.g., a cholera toxin, *Escherichia coli* heat-labile enterotoxin, liposome, immune-stimulating complex, immunostimulatory sequences oligodeoxynucleotides, or aluminum hydroxide or phosphate), and optionally, a pharmaceutically acceptable carrier (e.g., a phosphate buffered saline or a bicarbonate solution) or an excipient, (e.g., water, saline, dextrose, glycerol, ethanol, and combinations thereof) to form an immune composition. This immune composition can be formulated as an injectable, a liquid solution, or an emulsion. It may further contain minor amounts of auxiliary substances, such as a wetting or emulsifying agent and/or a pH buffering agent, to enhance its effectiveness in eliciting immune responses. The composition can also include a polymer that facilitates in vivo delivery. See Audran R. et al. Vaccine 21:1250-5, 2003; and Denis-Mize et al. Cell Immunol., 225:12-20, 2003.

The immune composition of this invention can be used for treating various diseases, depending upon the antigen contained therein (conjugated with the protein carrier). For example, it can elicit anti-cancer immune responses when the antigen is cancer-associated (e.g., sTn, Tn, or GM3). The immune composition can also be used for treating an infectious disease when it contains an antigen derived from a pathogen. The term "treating" as used herein refers to the application or administration of a composition including one or more active agents to a subject, who has a target disease, a symptom of the disease, or a predisposition toward the disease, with the purpose to cure, heal, alleviate, relieve, alter, remedy, ameliorate, improve, or affect the disease, the symptoms of the disease, or the predisposition toward the disease.

To treat a target disease, an effective amount of the immune composition of this invention is administered to a subject (e.g., a human) in need thereof via a suitable route. It can be administered parenterally, e.g., by intravenous, subcutaneous, or intramuscular injection, or via suppository or oral administration. Suppositories can contain binders and carriers such as polyalkalene glycols or triglycerides. Oral formulations may include normally employed incipients, such as pharmaceutical grades of saccharine, cellulose, magnesium carbonate and the like. These compositions take the form of solutions, suspensions, tablets, pills, capsules, sustained release formulations or powders and contain 10-95% of the immunoconjugate described herein.

The immune composition is administered in a manner compatible with the dosage formulation, and in an amount that is therapeutically effective, protective, and immunogenic. The quantity to be administered depends on the subject to be treated, including, for example, the capacity of the individual's immune system to synthesize antibodies, and if needed, to produce a cell-mediated immune response. Precise amounts of an active ingredient required to be administered depend on the judgment of the practitioner. However, suitable dosage ranges are readily determinable by one skilled in the art and may be of the order of micrograms of the immunoconjugate of this invention. Suitable regimes for initial administration and booster doses are also variable, but may include an initial administration followed by subsequent administrations. The dosage of the immune composition may also depend on the route of administration and varies according to the size of the host.

The immunoconjugate of this invention can also be used to generate antibodies in non-human mammals (for production of antibodies) or in humans (for treatment of diseases). Methods of making monoclonal and polyclonal antibodies and fragments thereof in animals are known in the art. See, e.g., Harlow and Lane, (1988) Antibodies: A Laboratory Manual, Cold Spring Harbor Laboratory, New York. The term "antibody" includes intact molecules as well as fragments thereof, such as Fab, F(ab')$_2$, Fv, scFv (single chain antibody), and dAb (domain antibody; Ward, et. al. (1989) Nature, 341, 544). These antibodies can be used for detecting a an antigen associated with a disease and subsequently, for disease diagnosis. They also can be used for treating the disease.

Polyclonal antibodies, heterogeneous populations of antibody molecules, are present in the sera of the immunized subjects. Monoclonal antibodies, homogeneous populations of antibodies to a polypeptide of this invention, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production. In addition, techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946,778 and 4,704,692) can be adapted to produce a phage library of single chain Fv antibodies. Single chain antibodies are formed by linking the heavy and light chain fragments of the Fv region via an amino acid bridge. Moreover, antibody fragments can be generated by known techniques. For example, such fragments include, but are not limited to, F(ab')$_2$ fragments that can be produced by pepsin digestion of an antibody molecule, and Fab fragments that can be generated by reducing the disulfide bridges of F(ab')$_2$ fragments. Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the invention. See, e.g., Green et al. (1994) Nature Genetics 7, 13; and U.S. Pat. Nos. 5,545,806 and 5,569,825.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Immunogenic Protein Carrier Preparation

A DNA fragment encoding seven tandem repeats of the cysteine-rich peptide Pro-Cys-Cys-Gly-Cys-Cys-Gly-Cys-Gly-Cys (SEQ ID NO: 1) was prepared by template-repeat PCR technology as described in Hsu et al., Cancer Research 60:3701-3705, 2000. The DNA fragment was further modified to create Bam HI and Hind III restriction sites at the 5' and 3' ends of the DNA fragment, respectively. It was then cloned into expression vectors containing a fragment encoding a His-tag and either a fragment encoding the Fc domain of rabbit IgG or a fragment encoding the Fc domain of mouse IgG. The resultant expression plasmids were capable of expressing fusion proteins including, from the N-terminus to the C-terminus, the rabbit or mouse Fc domain, the seven repeats of the cysteine-rich peptide, and two copies of a His-tag ("rFc-Cys-rich$_7$-H$_2$ protein carrier" and "mFc-Cys-rich$_7$-H$_2$ protein carrier").

The expression plasmids mentioned above were introduced into *E. coli* BL21(DE3)pLysS host cells for protein expression. Positive transformants were cultivated in a suitable medium at 37° C. and, when the OD595 values of the cultures reached 0.3, isopropyl β-D-1-thiogalactopyranoside was added to induce protein expression. The bacterial cells were further cultured for 1.5 hours and then harvested by centrifugation. The pellets thus obtained were lysed in a lysis buffer. The lysates were centrifuged and the supernatants were subjected to purification using nickle resins. The purified proteins were analyzed by SDS-PAGE using a 12.5% gel. Coomassie blue staining indicated that these proteins have a molecule weight of ~37 kD, close to the theoretic molecule weights of rFc-Cys-rich$_7$-H$_2$ and mFc-Cys-rich$_7$-H$_2$ protein carriers. Immunoblotting using either an anti-His-tag antibody or an anti-Fc antibody confirmed that the purified proteins are the protein carriers of interest.

Example 2

Immunoconjugate Preparation

Figure 3:
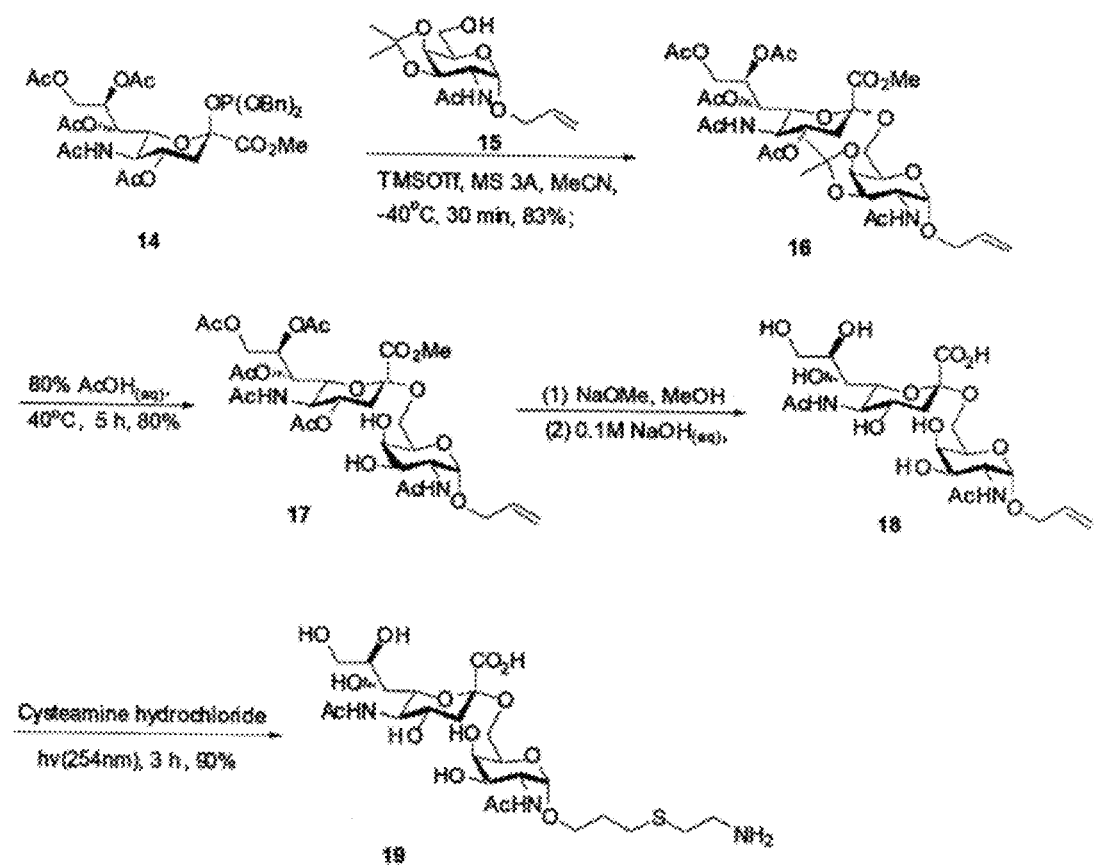
FIG. 3 is a synthetic scheme for chemical synthesis of sTn.
Figure 4:
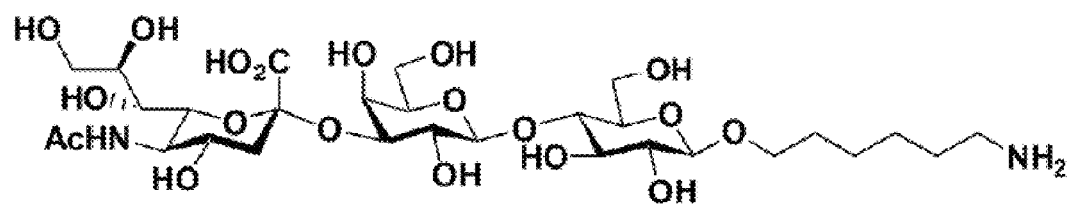
FIG. 4 is a diagram showing the structure of glycoepitope GM3.

Antigen sTn was synthesized following the synthetic route illustrated in FIG. 3. Briefly, the phosphite N-acetylneuraminic acid 14, prepared from neuraminic acid, was deprotected and coupled with the acetonide 15 to afford a 3:2 (α:β) mixture of the 1,6-linked sialoside 16 in 83% yield under the conventional conditions. The α/β anomers were separated after acidic deprotection of the corresponding acetonides. One of the anomers (17) was then further deprotected using NaOMe in MeOH and 0.1 M NaOH solution at room temperature to afford compound 18 (quant.). In order to attach the sTn to carrier proteins, the amine group was introduced onto the alkenyl moiety of 18 using photochemical activation with Cysteamine hydrochloride to provide 19 (90%), which was purified by a Biogel P2 column.

Antigen sTn, prepared by the method described above, conjugated with a linker containing a maleimide functional group (see FIG. 2, panel B), were mixed with the mFc-Cys-rich$_7$-H$_2$ protein carrier prepared by the method described in Example 1 above at various weight ratios (1:1, 2.5:1, and 5:1) to produce the mFc-Cys-rich$_7$-sTn immunoconjugate via a reaction between the maleimide group in the linker and a thio-group of a cysteine residue in the protein carrier. See FIG. 1, panel C.

Conjugation between the protein carrier and sTn was confirmed in a mobility shift assay. Briefly, the conjugates were subjected to SDS-PAGE using a 12.5% gel and then westernblot analysis using an anti-His-tag antibody. Results thus obtained showed that, after being conjugated with the sTn antigen, the protein carrier moved slower on the SDS-Polyacrymide gel, showing that its molecular weight was increased due to conjugation with sTn. As expected, one protein carrier molecule was found to be conjugated with multiple sTn molecule. Determined by the periodiate-thiobarbituric acid method, the conjugation efficiency was about 40%, which was much higher than that between sTn and KLH or BSA.

Example 3

Use of Immunoconjugate for Eliciting Antibody Production

Mice Immunization

Male Balb/c mice (8 weeks old) were injected subcutaneously with the mFc-Cys-rich$_7$-sTn immunoconjugate (containing 20 μg sTn), once every two weeks for three times. Sera were collected from the immunized mice each week and analyzed by dot blotting to examine presence of anti-sTn antibodies.

Male Balb/c mice (6-8 weeks old) were injected subcutaneously with an immunoconjugate containing the mFc-Cys-rich$_7$-H$_2$ carrier conjugated with GM3. The immunoconjugate was first suspended in complete Freund's adjuvant, which was switched to incomplete Freund's adjuvant two weeks later. Sera were collected from the immunized mice each week and subjected to dot blotting for examining presence of anti-GM3 antibodies.

Determination of Antibody Titers

Each serum sample obtained from the mice immunized with the mFc-Cys-rich$_7$-sTn immunoconjugate, diluted by 1000 fold with a TBS buffer (25 mM Tris-HCl pH8.0, 125 mM NaCl), was subjected to immunoblotting to determine the titer of anti-sTn antibodies contained therein as follows. sTn at various amounts (i.e., 30, 10, 3, 1, 0.3 and 0.1 μg) were dotted on a PVDF membrane (Millipore Immobion-PSQ ISEQ00010). The membrane was then incubated with the diluted serum sample under suitable conditions to allow binding of antibodies to the sTn antigen, washed to remove unbound antibodies, and then incubated with a labeled secondary antibody specific to mouse IgG. Results obtained from this study showed that sera obtained from the immunized mice all contain anti-sTn antibodies at high titers.

The anti-GM3 antibody titers of the sera obtained from the mice immunized with the mFc-Cys-rich$_7$-GM3 immunoconjugate were determined following the same method described above. All of the sera were found to contain anti-GM3 antibodies at high titers.

Determination of Antibody Specificity

The epitope specificity of the anti-sTn antibodies thus obtained was determined by a dot blotting assay as follows. Various amounts of GM3, a glycolipid mixture, a glycophospholipid mixture, and carbohydrate epitopes α-Tn, β-Tn, sTn, and N-acetylglucosamine were dotted on a PVDF membrane. The membrane was then incubated with a diluted serum sample (1000×) containing anti-sTn antibodies as described above under suitable conditions to allow binding of antibodies to their cognate antigens. Results show that the anti-sTn antibodies only bound to sTn, not to other antigens, indicating that these antibodies are highly specific to sTn.

Application of Anti-Tn Antibody in Cancer Diagnosis

Antigens Tn, sTn, and GM3, all associated with cancer, were conjugated with the mFc-Cys-rich$_7$-H$_2$ protein carrier following the method described above to form immunoconjugates. These immunoconjugates were used to immunize mice or rabbits to obtain mouse anti-Tn, anti-sTn and anti-GM3 antibodies and rabbit anti-Tn antibody.

The above-mentioned antibodies were applied in immunohistochemical (IHC) staining assays to examine the presence of Tn, sTn, or GM3 in tumor tissues. Briefly, fixed breast tumor tissue samples, placed on slides, were dewaxed in xylene and rehydrated in alcohol. The slides were incubated first in 0.01 mM citrate buffer (pH 6.0) at 95° C. for 40 minutes for antigen retrieval, then in 0.3% hydrogen peroxide for 30 minutes to block the activity of endogenous peroxidase, and finally in 5% normal horse serum in PBS for 30 minutes at room temperature to block nonspecific antibody reaction. After being washed with TBS supplemented with 0.1% Tween 20 (TBST), the slides were incubated with mouse anti-sTn antibody for 40 minutes at 4° C. The slides were then washed with TBST to remove unbound antibodies and incubated with HRP-conjugated anti-mouse IgG (SUPERPICTURE POLYMER KIT Zymed Laboratories, Inc.) for 10 minutes at room temperature. They were washed again with TBST to remove unbound antibodies and then incubated with DAB chromogen for signal development and also counterstained with Mayer's hematoxylin. Subsequently, the tissues on the slides were dehydrated and mounted. Results indicate that the mouse anti-sTn antibody, but not the pre-immune serum, recognized sTn expressed in breast tumor tissues.

The rabbit anti-Tn antibody, produced by the method described above, was used to examine the expression of Tn in cancer tissues obtained from 26 human patients having prostate cancer at different stages, applying the IHC assay described above. Positive staining signals were observed in the cancer tissues but not in normal cervical epithelium tissues. The intensities of the signal were found to be proportional to cancer malignancy.

The mouse anti-GM3 antibody mentioned above was used in an IHC assay and the results indicate that this antibody recognized GM3 expressed in tumor tissues.

Example 4

Anti-Cancer Effect of Anti-Tn Vaccine

The anti-cancer effect of a vaccine containing immunoconjugate mFc-Cys-rich$_7$-Tn and an adjuvant was examined in the Transgenic Adenocarcinoma of the Mouse Prostate (TRAMP) model. Male TRAMP mice (10-week old) were immunized with the vaccine once every two weeks for four times. Non-immunized TRAMP mice were used as controls. Results indicate that the control mice developed liver and kidney tumors while tumor development was not observed in the immunized mice. Further, the immunized mice survived much longer than the control mice. No Tn expression was observed in prostate tissues of the immunized mice in an IHC assay.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A non-naturally occurring polypeptide, comprising
an antigen presenting cell (APC) binding domain, and
a cysteine-rich domain that contains a fragment having the amino acid sequence of Pro-Cys-Cys-Gly-Cys-Cys-Gly-Cys-Gly-Cys (SEQ ID NO:1),
wherein the APC binding domain is an immunoglobulin (Ig) Fc fragment.

2. The polypeptide of claim 1, wherein the APC binding domain is a Fc fragment of a human Ig.

3. The polypeptide of claim 1, wherein the cysteine-rich domain contains 2 to 30 repeats of the fragment.

4. The polypeptide of claim 3, wherein the cysteine-rich domain contains 7 repeats of the fragment.

5. An immunoconjugate, comprising the polypeptide of claim 1 and an antigen, wherein the antigen is linked to a cysteine residue in the cysteine-rich domain.

6. The immunoconjugate of claim 5, wherein the antigen is linked to the cysteine residue via a linker.

7. The immunoconjugate of claim 6, wherein the antigen is a cancer-associated antigen.

8. The immunoconjugate of claim 7, wherein the antigen is a glycoantigen.

9. The immunoconjugate of claim 5, wherein the APC binding domain is a Fc fragment of a human Ig.

10. The immunoconjugate of claim 5, wherein the cysteine-rich domain contains 7 repeats of the fragment.

11. The immunoconjugate of claim 10, wherein the antigen is a cancer-associated antigen.

12. The immunoconjugate of claim 5, comprising two or more molecules of the antigen, each linked to a cysteine residue in the cysteine-rich domain.

13. An immune composition, comprising the immunoconjugate of claim 5 and an adjuvant.

14. A method of treating cancer, comprising administering to a subject in need thereof an effective amount of the immune composition of claim 13, wherein the antigen is a cancer-associated antigen.

15. The method of claim 14, wherein the antigen is a glycoantigen.

16. The method of claim 14, wherein the antigen is Tn, and the cancer is prostate cancer.

17. A method for inducing an immune response in a subject, comprising administering to the subject an effective amount of the immunoconjugate of claim 5.

18. The method of claim 17, wherein the antigen is a cancer-associated antigen.

19. The method of claim 17, wherein the APC binding domain is a Fc fragment of a human Ig.

20. The method of claim 17, wherein the cysteine-rich domain contains 7 repeats of the fragment.

21. The method of claim 20, wherein the antigen is a cancer-associated antigen.

22. The method of claim 17, wherein the immune response is secretion of an antibody that specifically binds to the antigen.

23. The method of claim 22, wherein the subject is a non-human mammal and the method further comprises isolating the antibody from the subject.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Artificial sequence
<220> FEATURE:
<223> OTHER INFORMATION: Synthetic peptide

<400> SEQUENCE: 1

```
Pro Cys Cys Gly Cys Cys Gly Cys Gly Cys
1               5                    10
```